(12) United States Patent
Schuler et al.

(10) Patent No.: US 12,016,619 B2
(45) Date of Patent: Jun. 25, 2024

(54) TRANSSEPTAL CROSSING SYSTEM FOR SINGLE PASS LARGE BORE ACCESS

(71) Applicant: CIRCA SCIENTIFIC, INC., Englewood, CO (US)

(72) Inventors: Brian Schuler, York, PA (US); Steve Howard, La Jolla, CA (US); Brad Klos, Solana Beach, CA (US)

(73) Assignee: CIRCA SCIENTIFIC, INC., Englewood, CO (US)

( * ) Notice: Subject to any disclaimer, the term of this patent is extended or adjusted under 35 U.S.C. 154(b) by 155 days.

(21) Appl. No.: 16/896,582

(22) Filed: Jun. 9, 2020

(65) Prior Publication Data

US 2021/0353355 A1    Nov. 18, 2021

Related U.S. Application Data

(60) Provisional application No. 63/024,986, filed on May 14, 2020.

(51) Int. Cl.
| | | |
|---|---|---|
| *A61B 18/14* | (2006.01) | |
| *A61B 18/12* | (2006.01) | |
| *A61B 18/00* | (2006.01) | |

(52) U.S. Cl.
CPC ...... *A61B 18/1487* (2013.01); *A61B 18/1206* (2013.01); *A61B 18/1492* (2013.01);
(Continued)

(58) Field of Classification Search
CPC ............ A61B 18/1487; A61B 18/1206; A61B 18/1492; A61B 2018/00077; A61B 2018/00083; A61B 2018/00178; A61B 2018/00351; A61B 2018/00357; A61B 2018/00369; A61B 2018/126;
(Continued)

(56) References Cited

U.S. PATENT DOCUMENTS 2,056,377 A    10/1936   Wappler
4,483,338 A    11/1984   Bloom et al.
(Continued)

FOREIGN PATENT DOCUMENTS

CN    2291901       9/1998
CN    105193476    12/2015
(Continued)

OTHER PUBLICATIONS

Clinical Analysis of RF Transseptal Puncture, NRG Transseptal Needle, USA, Canada, Baylis Medical Company, Inc., 2016.
(Continued)

*Primary Examiner* — Tigist S Demie
(74) *Attorney, Agent, or Firm* — Knobbe, Martens, Olson & Bear, LLP

(57) ABSTRACT

A single pass, large bore transseptal crossing catheter system is disclosed. An elongate, flexible tubular body has a proximal end, a distal end and an electrically conductive sidewall defining a central lumen. An insulation layer surrounds the sidewall and leaves exposed a first distal electrode tip. An inner conductive wire is provided, having a second distal electrode tip. The inner wire is axially movably extendable through the central lumen. A tubular insulation layer is provided in between the wire and the electrically conductive sidewall.

20 Claims, 9 Drawing Sheets

(52) U.S. Cl.
CPC .............. *A61B 2018/00077* (2013.01); *A61B 2018/00083* (2013.01); *A61B 2018/00178* (2013.01); *A61B 2018/00351* (2013.01); *A61B 2018/00357* (2013.01); *A61B 2018/00369* (2013.01); *A61B 2018/126* (2013.01); *A61B 2018/144* (2013.01); *A61B 2018/1475* (2013.01)

(58) Field of Classification Search
CPC ...... A61B 2018/144; A61B 2018/1475; A61B 18/16; A61B 2017/00247; A61B 2018/00702; A61B 2018/00726; A61B 2018/00767; A61B 2018/1253
See application file for complete search history.

(56) References Cited

U.S. PATENT DOCUMENTS

| | | | |
|---|---|---|---|
| 4,527,560 A * | 7/1985 | Masreliez | A61B 18/082 219/233 |
| 4,682,596 A | 7/1987 | Bales et al. | |
| 5,021,045 A | 6/1991 | Buckberg et al. | |
| 5,047,026 A * | 9/1991 | Rydell | A61B 18/1482 606/48 |
| 5,190,528 A | 3/1993 | Fonger et al. | |
| 5,221,281 A * | 6/1993 | Klicek | A61B 18/1487 606/45 |
| 5,304,171 A * | 4/1994 | Gregory | A61N 5/0601 606/15 |
| 5,348,554 A | 9/1994 | Imran et al. | |
| 5,417,687 A * | 5/1995 | Nardella | A61B 17/3476 604/164.08 |
| 5,431,649 A | 7/1995 | Mulier et al. | |
| 5,676,662 A * | 10/1997 | Fleischhacker | A61B 18/1492 600/374 |
| 5,676,670 A * | 10/1997 | Kim | A61B 17/320016 606/108 |
| 5,797,920 A * | 8/1998 | Kim | A61B 17/11 606/108 |
| 5,871,469 A * | 2/1999 | Eggers | A61B 18/1206 604/114 |
| 5,910,129 A * | 6/1999 | Koblish | A61M 25/0043 604/95.03 |
| 5,941,876 A * | 8/1999 | Nardella | A61B 18/1482 606/45 |
| 5,971,968 A | 10/1999 | Tu et al. | |
| 6,004,319 A * | 12/1999 | Goble | A61B 18/1206 606/48 |
| 6,012,457 A | 1/2000 | Lesh | |
| 6,024,740 A * | 2/2000 | Lesh | A61B 18/00 606/34 |
| 6,056,746 A * | 5/2000 | Goble | A61B 18/1482 606/48 |
| 6,074,386 A * | 6/2000 | Goble | A61B 18/1206 606/34 |
| 6,102,046 A * | 8/2000 | Weinstein | A61B 18/12 128/898 |
| 6,146,380 A | 11/2000 | Racz et al. | |
| 6,190,353 B1 | 2/2001 | Makower et al. | |
| 6,193,717 B1 | 2/2001 | Ouchi | |
| 6,231,546 B1 | 5/2001 | Milo et al. | |
| 6,251,107 B1 * | 6/2001 | Schaer | A61B 18/1492 600/374 |
| 6,391,005 B1 * | 5/2002 | Lum | A61B 5/053 600/506 |
| 6,475,226 B1 | 11/2002 | Belef et al. | |
| 6,529,756 B1 * | 3/2003 | Phan | A61B 18/1492 600/374 |
| 6,544,230 B1 | 4/2003 | Flaherty et al. | |
| 6,565,555 B1 | 5/2003 | Ryan et al. | |
| 6,565,562 B1 | 5/2003 | Shah et al. | |
| 6,602,248 B1 * | 8/2003 | Sharps | A61B 18/1402 606/32 |
| 6,645,199 B1 * | 11/2003 | Jenkins | A61B 18/1492 606/41 |
| 6,650,923 B1 | 11/2003 | Lesh et al. | |
| 6,723,094 B1 | 4/2004 | Desinger | |
| 6,936,024 B1 * | 8/2005 | Houser | A61B 18/1492 604/22 |
| 7,048,733 B2 | 5/2006 | Hartley et al. | |
| 7,070,596 B1 * | 7/2006 | Woloszko | A61B 18/1482 606/41 |
| 7,112,197 B2 | 9/2006 | Hartley et al. | |
| 7,150,747 B1 * | 12/2006 | McDonald | A61B 18/148 606/45 |
| 7,194,294 B2 | 3/2007 | Panescu et al. | |
| 7,229,437 B2 * | 6/2007 | Johnson | A61B 5/287 606/41 |
| 7,270,662 B2 | 9/2007 | Visram et al. | |
| 7,824,406 B2 | 11/2010 | Wang et al. | |
| 7,918,851 B2 | 4/2011 | Webster, Jr. et al. | |
| 7,947,040 B2 | 5/2011 | Davies et al. | |
| 8,092,450 B2 | 1/2012 | Davies et al. | |
| 8,192,425 B2 | 6/2012 | Mirza et al. | |
| 8,235,985 B2 | 8/2012 | Saadat et al. | |
| 8,457,714 B2 | 6/2013 | Shachar et al. | |
| 8,500,768 B2 | 8/2013 | Cohen | |
| 8,679,107 B2 | 3/2014 | Mirza et al. | |
| 8,834,384 B2 | 9/2014 | Krishnan | |
| 8,882,697 B2 * | 11/2014 | Celermajer | A61F 2/2442 604/8 |
| 8,992,556 B2 | 3/2015 | Chanduszko et al. | |
| 9,095,350 B2 | 8/2015 | Condie et al. | |
| 9,179,932 B2 | 11/2015 | Davies et al. | |
| 9,351,713 B2 * | 5/2016 | Hancock | A61B 10/04 |
| 9,415,188 B2 | 8/2016 | He et al. | |
| 9,504,398 B2 | 11/2016 | Krishnan | |
| 9,510,900 B2 | 12/2016 | Abou-Marie et al. | |
| 9,585,692 B2 | 3/2017 | Kurth et al. | |
| 9,597,146 B2 | 3/2017 | Davies et al. | |
| 10,166,070 B2 | 1/2019 | Davies et al. | |
| 10,172,632 B2 | 1/2019 | Morero et al. | |
| 10,183,151 B2 | 1/2019 | Alvarez et al. | |
| 10,485,569 B2 | 11/2019 | Lenker et al. | |
| 10,493,259 B2 | 12/2019 | Urbanski et al. | |
| 10,610,297 B2 | 4/2020 | Leung et al. | |
| 10,631,915 B1 | 4/2020 | Cosman | |
| 10,639,060 B2 | 5/2020 | Vardi et al. | |
| 10,716,920 B2 | 7/2020 | Kurth et al. | |
| 10,820,925 B2 | 11/2020 | Urbanski et al. | |
| 10,856,902 B2 | 12/2020 | Leeflang et al. | |
| 11,007,016 B2 | 5/2021 | Kusumoto | |
| 11,172,984 B2 | 11/2021 | Sharma et al. | |
| 11,583,312 B2 | 2/2023 | Howard et al. | |
| 11,751,905 B2 | 9/2023 | Howard et al. | |
| 11,819,241 B2 | 11/2023 | Howard et al. | |
| 2001/0056280 A1 * | 12/2001 | Underwood | A61B 18/148 606/41 |
| 2002/0058905 A1 | 5/2002 | Madrid et al. | |
| 2002/0095152 A1 * | 7/2002 | Ciarrocca | A61B 18/149 606/48 |
| 2002/0120259 A1 * | 8/2002 | Lettice | A61B 18/1492 606/32 |
| 2002/0177765 A1 * | 11/2002 | Bowe | A61B 18/1492 600/374 |
| 2002/0193781 A1 * | 12/2002 | Loeb | A61B 18/1402 606/15 |
| 2003/0009164 A1 * | 1/2003 | Woloszko | A61B 18/1492 606/41 |
| 2003/0083613 A1 | 5/2003 | Schaer | |
| 2003/0088245 A1 * | 5/2003 | Woloszko | A61B 18/148 606/41 |
| 2003/0109809 A1 | 6/2003 | Jen et al. | |
| 2003/0114833 A1 * | 6/2003 | Thompson | A61M 25/0147 604/528 |
| 2003/0163153 A1 | 8/2003 | Scheib | |
| 2004/0082860 A1 * | 4/2004 | Haissaguerre | A61B 5/287 600/466 |
| 2004/0133113 A1 | 7/2004 | Krishnan | |
| 2004/0143261 A1 | 7/2004 | Hartley et al. | |
| 2004/0143262 A1 | 7/2004 | Visram et al. | |

(56) References Cited

U.S. PATENT DOCUMENTS

| | | | |
|---|---|---|---|
| 2004/0167509 A1* | 8/2004 | Taimisto | A61B 18/1492 606/41 |
| 2004/0186469 A1* | 9/2004 | Woloszko | A61B 5/015 606/41 |
| 2004/0220461 A1 | 11/2004 | Schwartz | |
| 2004/0220462 A1 | 11/2004 | Schwartz | |
| 2005/0033288 A1 | 2/2005 | Auth et al. | |
| 2005/0065498 A1 | 3/2005 | McFerran | |
| 2005/0149097 A1 | 7/2005 | Regnell et al. | |
| 2005/0154386 A1 | 7/2005 | West et al. | |
| 2005/0171478 A1 | 8/2005 | Selmon et al. | |
| 2005/0215994 A1 | 9/2005 | Solomon | |
| 2006/0074484 A1 | 4/2006 | Huber | |
| 2006/0079873 A1* | 4/2006 | Scopton | A61M 25/0069 604/22 |
| 2006/0178666 A1 | 8/2006 | Cosman et al. | |
| 2006/0241583 A1 | 10/2006 | Malecki et al. | |
| 2006/0287650 A1* | 12/2006 | Cao | A61B 18/1492 606/41 |
| 2007/0016182 A1* | 1/2007 | Lipson | A61B 18/12 606/34 |
| 2007/0073389 A1 | 3/2007 | Bolduc et al. | |
| 2008/0119846 A1* | 5/2008 | Rioux | A61B 18/1482 606/41 |
| 2008/0140073 A1 | 6/2008 | Schwartz | |
| 2008/0154259 A1* | 6/2008 | Gough | A61B 18/18 606/41 |
| 2008/0208184 A1* | 8/2008 | Davies | A61B 18/1492 606/34 |
| 2008/0215085 A1* | 9/2008 | Whisenant | A61B 18/1492 606/213 |
| 2009/0005774 A1* | 1/2009 | Fernald | A61B 18/1482 606/41 |
| 2009/0012517 A1 | 1/2009 | de la Rama et al. | |
| 2009/0093803 A1* | 4/2009 | Herrin | A61B 18/1492 606/33 |
| 2009/0099555 A1* | 4/2009 | Viohl | A61N 1/37 606/1 |
| 2010/0191142 A1 | 7/2010 | Paul et al. | |
| 2011/0112564 A1 | 5/2011 | Wolf | |
| 2011/0166519 A1* | 7/2011 | Nguyen | A61N 1/403 604/114 |
| 2011/0224666 A1 | 9/2011 | Davies et al. | |
| 2012/0232546 A1 | 9/2012 | Mirza et al. | |
| 2013/0046305 A1* | 2/2013 | Davies | A61B 18/1492 606/45 |
| 2013/0317528 A1 | 11/2013 | Anderson et al. | |
| 2014/0039492 A1* | 2/2014 | Long | A61B 18/1477 606/41 |
| 2014/0066917 A1* | 3/2014 | Cosman, Jr. | A61B 18/18 606/33 |
| 2014/0100561 A1* | 4/2014 | Biadillah | A61B 18/18 606/33 |
| 2014/0107644 A1 | 4/2014 | Falwell et al. | |
| 2014/0121658 A1* | 5/2014 | Cosman, Jr. | A61B 18/1477 606/33 |
| 2014/0142607 A1 | 5/2014 | Cage et al. | |
| 2014/0206987 A1 | 7/2014 | Urbanski et al. | |
| 2014/0228841 A1* | 8/2014 | Davies | A61B 18/1492 606/45 |
| 2014/0364844 A1* | 12/2014 | Van Wyk | A61B 18/1477 606/37 |
| 2015/0141978 A1 | 5/2015 | Subramaniam et al. | |
| 2015/0157353 A1 | 6/2015 | Lenker et al. | |
| 2015/0173827 A1* | 6/2015 | Bloom | A61B 18/148 606/39 |
| 2015/0182255 A1 | 7/2015 | Shivkumar | |
| 2015/0223866 A1* | 8/2015 | Buelna | A61K 31/045 600/3 |
| 2015/0265337 A1* | 9/2015 | Bloom | A61B 18/1485 606/48 |
| 2015/0265344 A1 | 9/2015 | Aktas et al. | |
| 2015/0297246 A1* | 10/2015 | Patel | A61B 17/3478 606/79 |
| 2016/0045219 A1 | 2/2016 | Guala et al. | |
| 2016/0235469 A1* | 8/2016 | Prisco | A61B 18/1485 |
| 2016/0262795 A1 | 9/2016 | Urbanski et al. | |
| 2016/0374751 A1* | 12/2016 | Davies | A61B 18/1477 606/48 |
| 2017/0071667 A1* | 3/2017 | Leung | A61B 90/39 |
| 2017/0135559 A1 | 5/2017 | Horrisberger et al. | |
| 2017/0348049 A1* | 12/2017 | Vrba | A61B 18/1492 |
| 2017/0360498 A1 | 12/2017 | Davies et al. | |
| 2018/0028258 A1 | 2/2018 | Zamarripa et al. | |
| 2018/0064415 A1 | 3/2018 | Zhai et al. | |
| 2018/0064915 A1 | 3/2018 | Kurth et al. | |
| 2018/0070982 A1 | 3/2018 | Kimmel et al. | |
| 2018/0133460 A1 | 5/2018 | Townley et al. | |
| 2018/0146839 A1* | 5/2018 | Friedlander | A61B 1/0005 |
| 2018/0263658 A1 | 9/2018 | Drasler | |
| 2018/0289388 A1* | 10/2018 | Lenker | A61B 18/1477 |
| 2018/0333162 A1 | 11/2018 | Saab | |
| 2019/0125422 A1 | 5/2019 | Babkin et al. | |
| 2019/0134349 A1 | 5/2019 | Cohn et al. | |
| 2019/0274581 A1 | 9/2019 | Mosesov | |
| 2019/0336198 A1 | 11/2019 | Viswanathan et al. | |
| 2019/0374254 A1* | 12/2019 | Arevalos | A61B 17/32053 |
| 2019/0374281 A1* | 12/2019 | Davies | A61B 18/1492 |
| 2020/0008869 A1* | 1/2020 | Byrd | A61B 18/1206 |
| 2020/0038091 A1* | 2/2020 | Cao | A61B 18/14 |
| 2020/0060710 A1 | 2/2020 | Urbanski et al. | |
| 2020/0196908 A1 | 6/2020 | Ben-Haim et al. | |
| 2020/0352647 A1* | 11/2020 | Davies | A61B 17/3478 |
| 2021/0038892 A1 | 2/2021 | Velasco Valcke | |
| 2021/0068892 A1* | 3/2021 | Urbanski | A61B 5/4836 |
| 2021/0077419 A1* | 3/2021 | Buelna | A61B 18/1492 |
| 2021/0121227 A1 | 4/2021 | Davies et al. | |
| 2021/0353354 A1 | 11/2021 | Schuler et al. | |
| 2021/0353356 A1 | 11/2021 | Schuler et al. | |
| 2021/0401483 A1 | 12/2021 | Highsmith et al. | |
| 2022/0061884 A1 | 3/2022 | Howard et al. | |
| 2022/0061909 A1 | 3/2022 | Howard et al. | |
| 2022/0061911 A1 | 3/2022 | Howard et al. | |
| 2022/0110577 A1 | 4/2022 | Highsmith et al. | |
| 2022/0354533 A1 | 11/2022 | Lenker | |
| 2023/0093231 A1 | 3/2023 | Howard et al. | |

FOREIGN PATENT DOCUMENTS

| | | | |
|---|---|---|---|
| EP | 2037812 | 3/2009 | |
| JP | WO2018163899 A1 * | 9/2018 | A61N 1/05 |
| WO | WO 2002/058780 | 8/2002 | |
| WO | WO 2005/046487 | 5/2005 | |
| WO | WO 2008/008796 | 1/2008 | |
| WO | WO 2013/101632 | 7/2013 | |
| WO | WO 2014/089373 | 6/2014 | |
| WO | WO 2018/165277 | 9/2018 | |
| WO | WO 2021/014316 | 1/2021 | |
| WO | WO 2021/231465 | 11/2021 | |
| WO | WO 2022/046777 | 3/2022 | |

OTHER PUBLICATIONS

International Search Report and Written Opinion, Application No. PCT/US2021/031827, dated Oct. 20, 2021.

International Search Report and Written Opinion in corresponding International Patent Application No. PCT/US2021/047361, mailed Jan. 27, 2022, in 10 pages.

U.S. Appl. No. 16/896,582, filed Jun. 9, 2020, *Transseptal Crossing System for Single Pass Large Bore Access*.

U.S. Appl. No. 16/896,604, filed Jun. 9, 2020, *Tubular Large Bore Transseptal Crossing Sheath*.

U.S. Appl. No. 16/896,648, filed Jun. 9, 2020, *Method for Single Pass Large Bore Transseptal Crossing*.

\* cited by examiner

TRANSSEPTAL CROSSING SYSTEM FOR SINGLE PASS LARGE BORE ACCESS

CROSS-REFERENCE TO RELATED APPLICATIONS

This application claims the priority benefit under 35 U.S.C. § 119(e) of U.S. Provisional Application No. 63/024,986, filed May 14, 2020, the entirety of which is hereby incorporated by reference herein.

BACKGROUND OF THE INVENTION

Transseptal crossing is used to access the left atrium crossing from the right atrium through the septal wall for any of a variety of electrophysiology (EP) or structural heart procedures. For example, the left atrium is routinely accessed to assess hemodynamics and/or perform mitral valvuloplasty, or to accommodate transvascular atrial fibrillation (AF) ablation procedures.

Crossing the septum normally requires locating and puncturing the fossa ovalis to access the left atrium. Locating the fossa ovalis may be accomplished using fluoroscopy and ultrasound, and potentially echocardiography.

Mechanical puncture through the tissue of the fossa ovalis can be accomplished using a piercing tool such as a standard Brockenbrough needle as is understood in the art. Alternatively, a transseptal needle having a radio frequency energized tip may be used, such as those produced by Baylis Medical Company, Inc.

The foregoing devices and techniques have proven useful in a variety of EP and structural heart procedures, in which the procedural access sheath is often no larger than about 3.667 mm (11 French). However, a growing number of procedures such as left atrial appendage occlusion device implantation and various Mitral valve replacement or repair require "large bore" access, which is not possible using the above techniques alone.

Instead, traditional transseptal puncture is normally carried out with small bore sheaths ranging from 8 Fr to 11 Fr which are then exchanged over stiff guidewires for the large bore sheaths with outer dimensions as large as 24 Fr in the case of the MitraClip Steerable Guide Catheter. Dilators for the transseptal sheaths usually accommodate 0.032 in. wires, however Baylis has introduced a small bore transseptal sheath with a dilator that accommodates a 0.035 in. wire. Regardless of the transseptal sheath, the operator must utilize a number of additional pieces of equipment including the small bore transseptal sheath and dilator, and often a 0.025 in. "stiff" pigtail wire (Baylis, Toray) to use as a rail to drive the small bore transseptal sheath and dilator before switching to a 0.035 in. guidewire (Amplatz extra stiff or Safari) to drive the large bore sheath safely into the LA. The entire small bore sheath must be driven into the LA to make the switch to the appropriate stiff 0.035 in. guidewire to drive the large bore sheath.

Thus, there remains a need for a transseptal crossing system that is based upon a 0.035 inch guidewire access, that enables single pass crossing of larger sheaths, such as the Boston Scientific Watchman guide sheath, Medtronic Flex-cath and others known in the art or yet to be released.

SUMMARY OF THE INVENTION

In general, the present invention provides a single pass transseptal crossing device, for enabling large bore access in a single pass. The system includes an insulated cannula with a conductive tip positionable through the dilator of a large bore sheath. The tip of the cannula is expressed distal to the tip of the dilator. The insulated cannula can serve as an electrical conduit of RF energy. The cannula can be energized to deliver RF energy directly to tissues and/or through a separate conductive wire or obturator. An insulated wire or obturator can thus be independently energized or can be energized passively via the energized cannula. The cannula may be 0.050" outer diameter (OD) and approximately 0.038" inner diameter (ID) allowing delivery of a 0.035" wire which together (stiff 0.035 wire and 0.050 cannula) creates a sturdy rail to drive large bore dilators and sheaths in a single pass. The tip of the cannula can be scalloped to deliver high density current to the scalloped edges for improved cutting. The system permits irrigation with hypotonic saline or D5W to preferentially drive current through the myocardium.

Thus, there is provided in accordance with one aspect of the present invention a single pass, large bore transseptal crossing catheter, such as for accessing the left atrium of the heart. The catheter comprises an elongate, flexible tubular body, having a proximal end, a distal end and an electrically conductive sidewall defining a central lumen. An insulation layer surrounds the sidewall and leaving exposed a first distal electrode tip. An inner conductive wire having a second distal electrode tip, is axially movably extendable through the central lumen. A tubular insulation layer is provided in between the wire and the electrically conductive sidewall.

The first distal electrode tip may comprise an annular conductive surface at the distal end of the tubular body. The second distal electrode tip may be concentrically extendable through the annular conductive surface. The first distal electrode tip may comprise at least one distal projection, or at least two or three projections and in one implementation comprises a scalloped distal edge.

The second distal electrode may comprise a smooth, hemispherical surface, or may be provided with a sharpened distally facing projection. The catheter may additionally comprise an annular lumen extending between the tubular body and the wire, from the proximal hub to an exit port at the distal end.

In accordance with a further aspect of the present invention, there is provided an introducer sheath, for enabling a single pass, large bore transseptal crossing. The introducer sheath comprises an elongate, flexible tubular body, having a proximal end, a distal end and an electrically conductive sidewall defining a central lumen. A tubular insulation layer may surround the sidewall, leaving exposed an annular conductive surface at the distal end. A proximal hub may be provided on the tubular body, having at least one access port in communication with the central lumen. A connector may be carried by the proximal end, in electrical communication with the conductive sidewall. The distal conductive surface may comprise at least one distal projection, or at least two or three projections and in one implementation comprises a scalloped distal edge.

There is also provided a method of accessing the left atrium with a large bore catheter in a single pass. The method comprises providing a single pass, large bore transseptal crossing catheter; positioning the distal end in contact with a fossa ovalis; and energizing the distal end to enable passage of the distal end into the left atrium.

The energizing step may comprise energizing a first distal electrode tip on a conductive tubular cannula and/or energizing a second distal electrode tip on an RF core wire. The first and second distal electrode tips may be energized in a bipolar mode.

The method may comprise accessing the left atrium, energizing the second distal electrode tip, advancing the wire through the fossa ovalis, thereafter energizing the first distal electrode tip and advancing the cannula into the left atrium.

A large bore access sheath may thereafter be advanced over the transseptal crossing catheter and into the left atrium, and the transseptal crossing catheter may then be removed, leaving the large bore access sheath extending into the left atrium.

An index procedure catheter may be advanced through the large bore access sheath and into the left atrium. The index procedure catheter may be configured to deliver a left atrial appendage implant such as an occlusion device, or to accomplish a mitral valve repair or replacement.

BRIEF DESCRIPTION OF THE DRAWINGS

FIG. 2A is a cross section taken along the line A-A in FIG. 2.

FIG. 2B is a detail view of the distal tip of the needle in FIG. 2.

DETAILED DESCRIPTION OF THE PREFERRED EMBODIMENT

Figure 1:
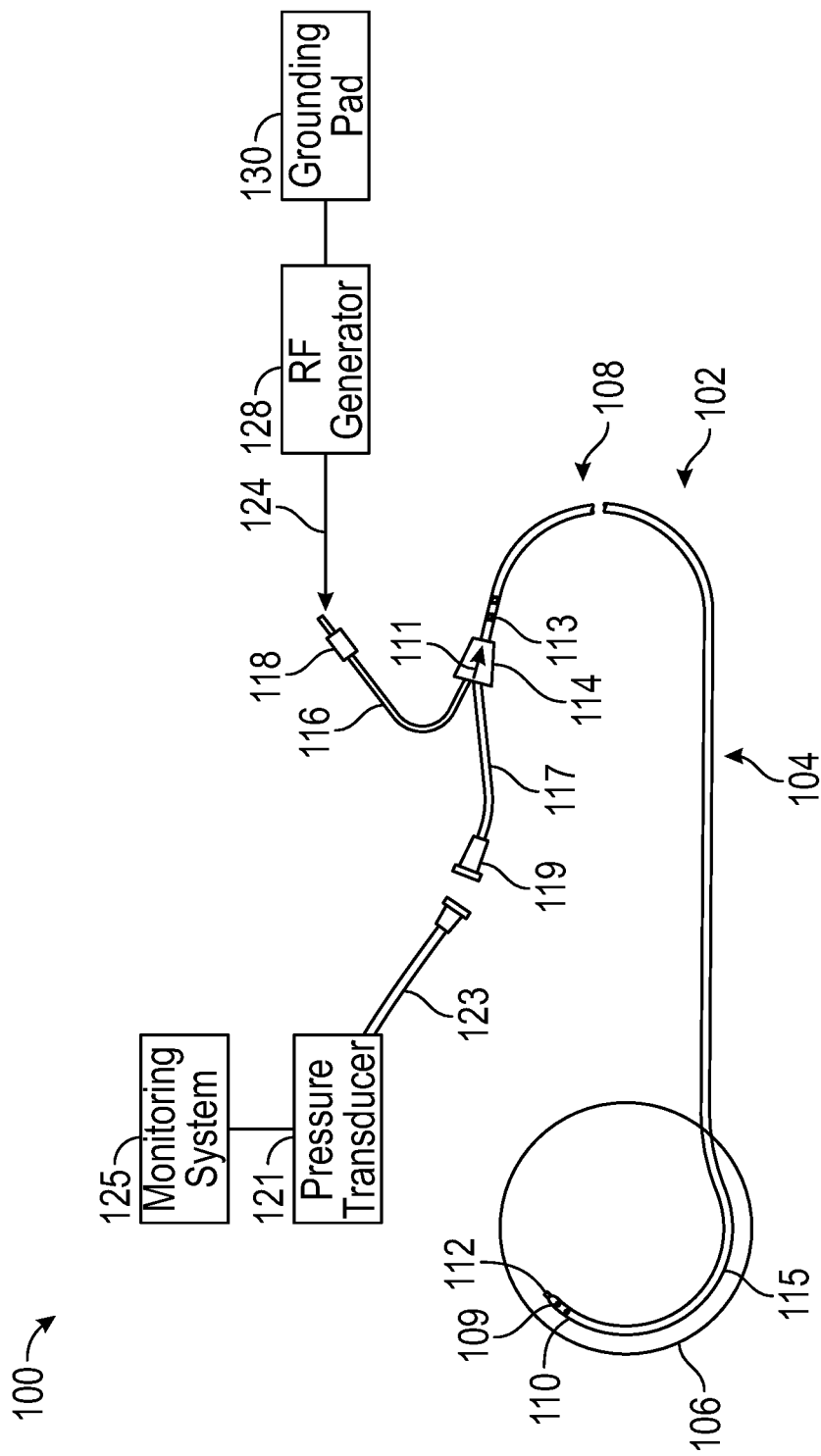
FIG. 1 schematically illustrates a transseptal crossing system in accordance with the present invention.

FIG. 1 illustrates an embodiment of a tissue penetrating apparatus 102 in a transseptal crossing system 100. Apparatus 102 comprises an elongate tubular body 104 having a distal region 106, and a proximal region 108. Distal region 106 is adapted to be inserted within and along a lumen of a body of a patient, such as a patient's vasculature, and maneuverable therethrough to a desired location proximate material, such as tissue, to be perforated.

In some embodiments, the tubular body 104 may have at least one lumen extending from proximal region 108 to distal region 106 such as lumen 208 shown in FIG. 2A. Tubular body 104 may be constructed of a biocompatible polymer material jacket typically with a metal core that provides column strength to apparatus 102. The tubular body 104 is sufficiently stiff to permit a dilator 84 and a large bore guiding sheath 12 (See FIG. 6) to be easily advanced over apparatus 102 and through a perforation. Examples of suitable materials for the tubular portion of tubular body 104 are stainless steel, nitinol, polyetheretherketone (PEEK), nylon, and polyimide. In the illustrated embodiment, the outer diameter along the tubular portion of tubular body 104 may taper down to distal region 106. In alternate embodiments, the outer diameter along tubular body 104 remains substantially constant from proximal region 108 to distal region 106.

Distal region 106 comprises a softer polymer material with an optional embedded braid or coil so that it is pliable and atraumatic when advanced through vasculature. In some embodiments, the material is also formable (e.g., Nitinol or stainless steel with a polymer jacket), so that its shape can be changed during manufacturing, typically by exposing it to heat while it is fixed in a desired shape. In an alternate embodiment, the shape of distal region is modifiable by the operator during use. An example of a suitable plastic is PEBAX (a registered trademark of Atofina Chemicals, Inc.). In the present embodiment, the distal region 106 comprises a curve portion 115.

As the distal region 106 is advanced out of a guiding sheath, it may have a preset curve so that it curls away from the general axis of the sheath which helps ensure that energy delivery tip 112 is not in a position to inadvertently injure unwanted areas within a patient's heart after trans-septal perforation. Curve length may be about 4 cm (about 1.57") to about 6 cm (about 2.36") and the curve may traverse about 225 to about 315 degrees of the circumference of a circle. For example, the curve may be about 5 cm in length and may traverse about 270 degrees of the circumference of a circle. Such an embodiment may be useful to avoid unwanted damage to cardiac structures.

In some embodiments, curve portion 115 begins about 0.5 cm to about 1.5 cm proximal to energy delivery device 112, leaving an approximately 1 cm (about 0.39") straight portion in the distal region 106 of apparatus 102. This ensures that this initial portion of apparatus 102 will exit dilator 84 (see FIG. 6) without curving, enabling the operator to easily position the apparatus 102, for example, against a septum as described further below. This feature further ensures that the distal region 106 of apparatus 102 will not begin curving within the atrial septum.

Distal region 106 may have a smaller outer diameter compared to the remainder of tubular body 104 so that dilation of a perforation is limited while the distal region 106 is advanced through the perforation. Limiting dilation seeks to ensure that the perforation will not cause hemodynamic instability once apparatus 102 is removed. In some embodiments, the outer diameter of distal region 106 may be no larger than about 0.8 mm to about 1.0 mm. For example, the outer diameter of distal region 106 may be about 0.9 mm (about 0.035"). This is comparable to the distal outer diameter of the trans-septal needle that is traditionally used for creating a perforation in the atrial septum. Similarly, in some embodiments, the outer diameter of tubular body 104 may be no larger than about 0.040" to about 0.060". For example, the outer diameter of tubular body 104 may be about 0.050" (1.282 mm), which is also comparable to the trans-septal needle dimensions.

Distal region 106 terminates at functional tip region 110, which comprises an energy delivery component and optionally also as an ECG measuring device. Functional tip region 110 comprises at least one energy delivery tip 112 made of a conductive and optionally radiopaque material, such as stainless steel, tungsten, platinum, or another metal. One or more radiopaque markings may be affixed to tubular body 104 to highlight the location of the transition from distal region 106 to the remainder of tubular body 104, or other important landmarks on apparatus 102. Alternately, the entire distal region 106 of apparatus 102 may be radiopaque. This can be achieved by filling the polymer material, for example PEBAX, used to construct distal region 106 with radiopaque filler. An example of suitable radiopaque filler is Bismuth. Distal region 106 may contain at least one opening 109 which is in fluid communication with main lumen 200 (FIG. 2A) as described further below.

In the illustrated embodiment, proximal region 108 comprises a hub 114, to which are attached a catheter connector cable 116, and connector 118. Tubing 117 and adapter 119 are attached to hub 114 as well. Proximal region 108 may also have one or more depth markings 113 to indicate distances from functional tip region 110, or other important landmarks on apparatus 102. Hub 114 comprises a curve direction or orientation indicator 111 that is located on the same side of apparatus 102 as the curve 115 in order to indicate the direction of curve 115. Orientation indicator 111 may comprise inks, etching, or other materials that enhance visualization or tactile sensation. One or more curve direction indicators may be used and they may be of any suitable shape and size and a location thereof may be varied about the proximal region 108.

In the illustrated embodiment, adapter 119 is configured to releaseably couple apparatus 102 to an external pressure transducer 121 via external tubing 123. External pressure transducer 121 is coupled to a monitoring system 125 that converts a pressure signal from external pressure transducer 121 and displays pressure as a function of time. Catheter connector cable 116 may connect to an optional Electrocardiogram (ECG) interface unit via connector 118. An optional ECG connector cable connects an ECG interface unit to an ECG recorder, which displays and captures ECG signals as a function of time. A generator connector cable may connect the ECG interface unit to an energy source such as a generator (not illustrated). In this embodiment, the ECG interface unit can function as a splitter, permitting connection of the electrosurgical tissue piercing apparatus 102 to both an ECG recorder and generator simultaneously. ECG signals can be continuously monitored and recorded and the filtering circuit within the ECG interface unit and may permit energy, for example RF energy, to be delivered from generator 128 through electrosurgical apparatus 102 without compromising the ECG recorder.

In another embodiment (not shown) of apparatus 102, there may be a deflection control mechanism associated with the distal region 106 of apparatus 102 and an operating mechanism to operate said control mechanism associated with the proximal region 108 of apparatus 102. One or two or more pull wires may extend from a proximal control to the distal region 106 to actively deflect the distal region 106 as will be understood in the art. The control mechanism may be used to steer or otherwise actuate at least a portion of distal region 106.

Generator 128 may be a radiofrequency (RF) electrical generator that is designed to work in a high impedance range. Because of the small size of energy delivery tip 112, the impedance encountered during RF energy application is very high. General electrosurgical generators are typically not designed to deliver energy in these impedance ranges, so only certain RF generators can be used with this device. In one embodiment, the energy is delivered as a continuous wave at a frequency between about 400 kHz and about 550 kHz, such as about 460 kHz, a voltage of between 100 to 200 V RMS and a duration of up to 99 seconds. A grounding pad 130 is coupled to generator 128 for attaching to a patient to provide a return path for the RF energy when generator 128 is operated in a monopolar mode.

Other embodiments could use pulsed or non-continuous RF energy. Some embodiments for pulsed radio frequency energy have radio frequency energy of not more than about 60 watts, a voltage from about 200 Vrms to about 400 Vrms and a duty cycle of about 5% to about 50% at about from slightly more than 0 Hz to about 10 Hz. More specific embodiments include radio frequency energy of not more than about 60 watts, a voltage from about 240 Vrms to about 300 Vrms and a duty cycle of 5% to 40% at 1 Hz, with possibly, the pulsed radio frequency energy being delivered for a maximum of 10 seconds. In one example, the generator can be set to provide pulsed radio frequency energy of not more than about 50 watts, a voltage of about 270 Vrms, and a duty cycle of about 10% at 1 Hz. Alternatively, the pulsed radio frequency energy could comprise radio frequency energy of not more than about 50 watts, a voltage of about 270 Vrms, and a duty cycle of about 30% at 1 Hz.

In still other embodiments of apparatus 102, different energy sources may be used, such as radiant (e.g. laser), ultrasound, thermal or other frequencies of electrical energy (e.g. microwave), with appropriate energy sources, coupling devices and delivery devices depending upon the desired clinical performance.

Figure 2:
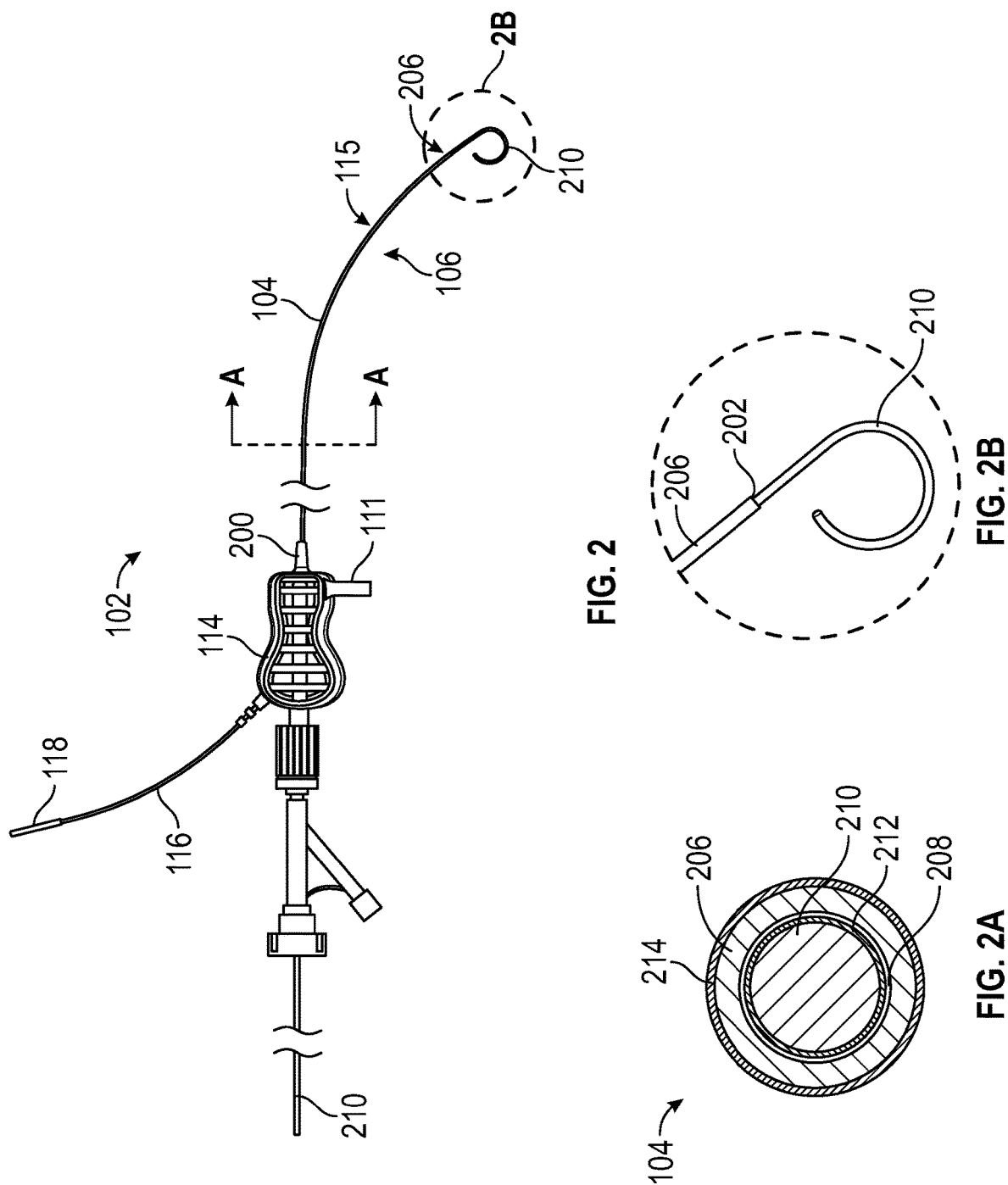
FIG. 2 is a side elevational view of an RF needle in accordance with the present invention.

Additional details of the tissue penetration apparatus 102 are described in connection with FIG. 2. Referring to FIGS. 2 and 2A, the tubular body 104 comprises a cannula 206 such as a 0.050" cannula having a central lumen 208 extending therethrough. The lumen 208 is dimensioned to slidably receive a guide wire 210 such as an 0.035" guidewire. In certain implementations of the invention, it may be desirable to electrically isolate the guide wire 210 from the cannula 206. This may be accomplished by providing a tubular insulation layer 212 positioned between the guide wire 210 and the cannula 206. In the illustrated embodiment, the insulation layer 212 comprises a coating or tubular sleeve surrounding the guide wire 210. A further tubular insulation layer 214 may be provided on the outside of the cannula 206 to electrically isolate the cannula 206 from the patient.

Referring to FIG. 2B, there is illustrated a detail view of the distal end 202 of cannula 206, having a guide wire 210 extending therethrough. The guide wire 210 may comprise a pigtail or other curved distal end as is understood in the art.

Figure 3:
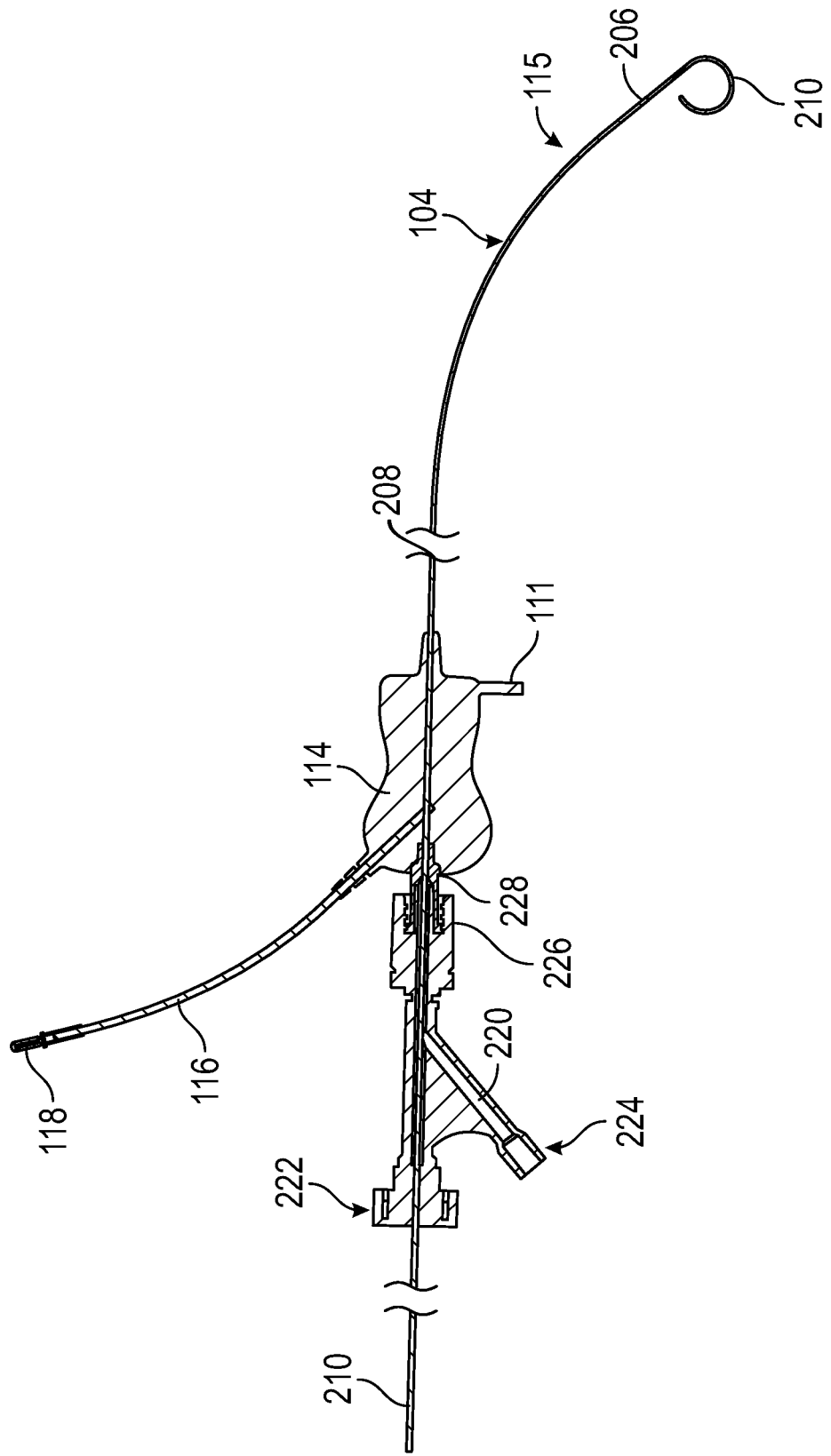
FIG. 3 is a cross sectional view through the needle of FIG. 2.

Referring to FIG. 3, the tissue penetrating apparatus 102 may additionally be provided with a Y connector 220, having a proximal guide wire access port 222 and a flush port 224 in communication with the distal region 106 such as via exit port 109 (FIG. 1) or cannula 206 central lumen 208. The Y connector 220 may be provided with a distal first connector 226 configured to cooperate with a second complementary connector 228 on the proximal end of the hub 114. First connector 226 and second connector 228 may be complementary components of a standard luer connector as is understood in the art. Alternatively, the hub 114 and Y connector 220 may be formed as an integral unit.

Figure 4A:
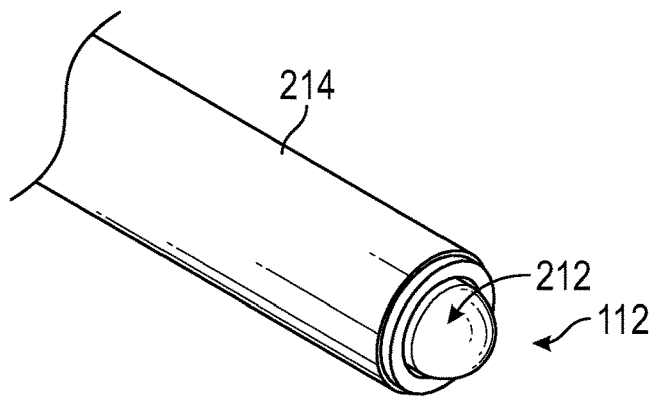
FIG. 4A-4C are detail views of the distal energy delivery tip of one implementation of the invention.
Figure 4B:
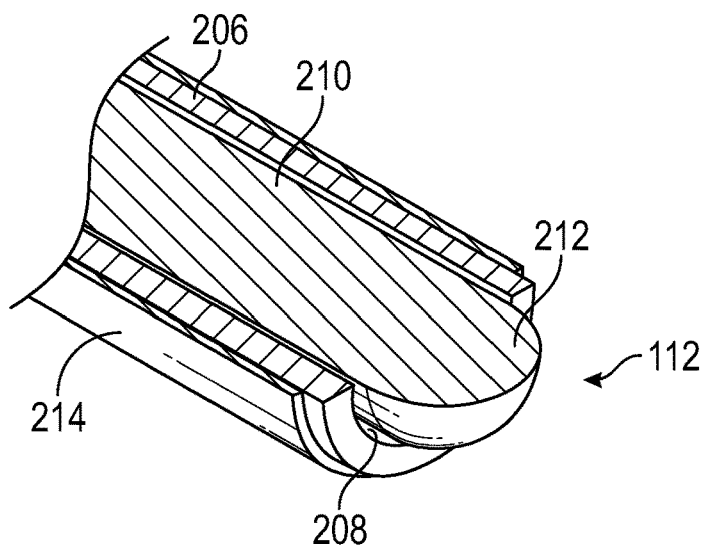
Figure 4C:
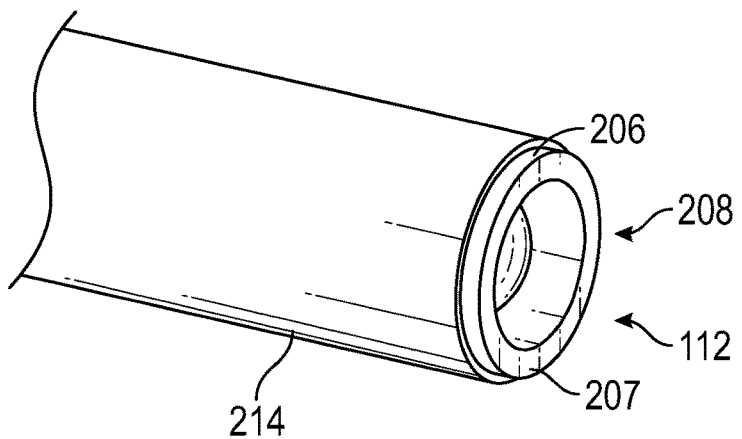

FIGS. 4A-4C illustrate the axial slidability of the guidewire 210 within the cannula 206. In FIG. 4C, the guidewire has been proximally retracted into the central lumen 208 so that the leading surface of the system is an annular charge transfer surface 207, which comprises a distal end face of the cannula 206. The insulation layer 214 on cannula 206 may extend distally all the way to the edge of the end face of the cannula 206, or to no more than 2 mm or 1 mm or less proximally of the end face of the cannula 206. The system thus permits delivering RF energy from either the guidewire alone, or the cannula alone or both, depending upon the desired clinical performance.

The separately insulated cannula 206 and guidewire can be configured to deliver bipolar electricity to the distal tip. The cannula 206 can be used as the ground path and replace the body pad or other electrode, which may provide desirable impedance characteristics depending upon the desired clinical performance.

Figure 5A:
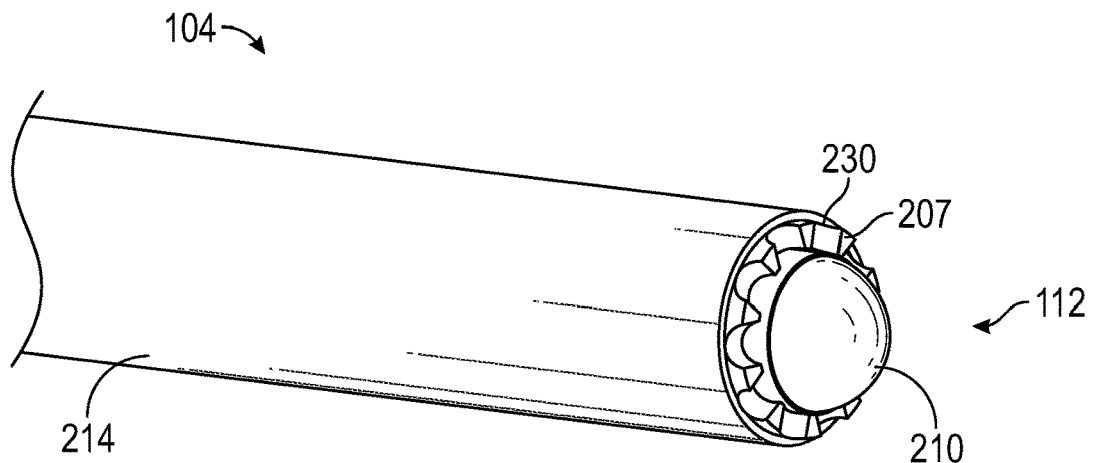
FIG. 5A-5C are detail views of the distal energy delivery tip of another implementation of the invention.
Figure 5B:
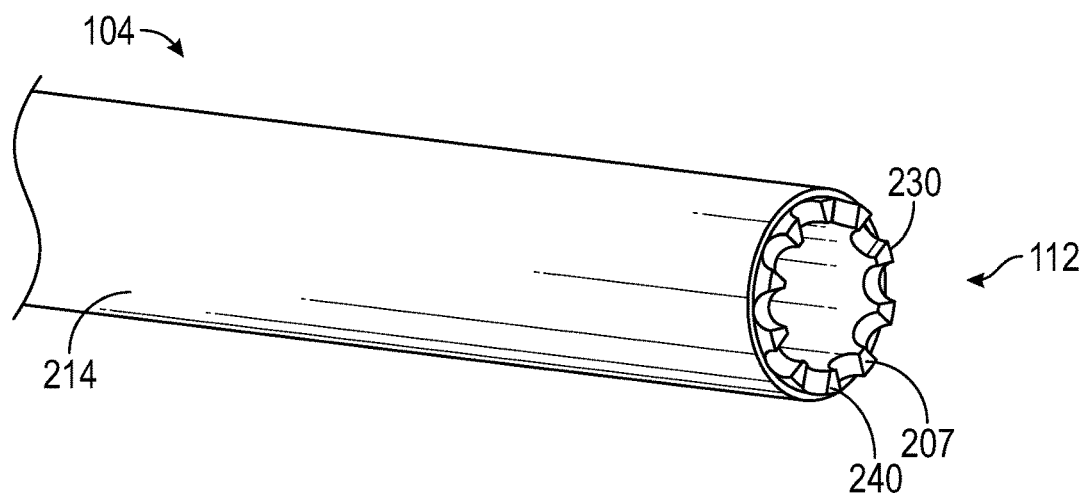
Figure 5C:
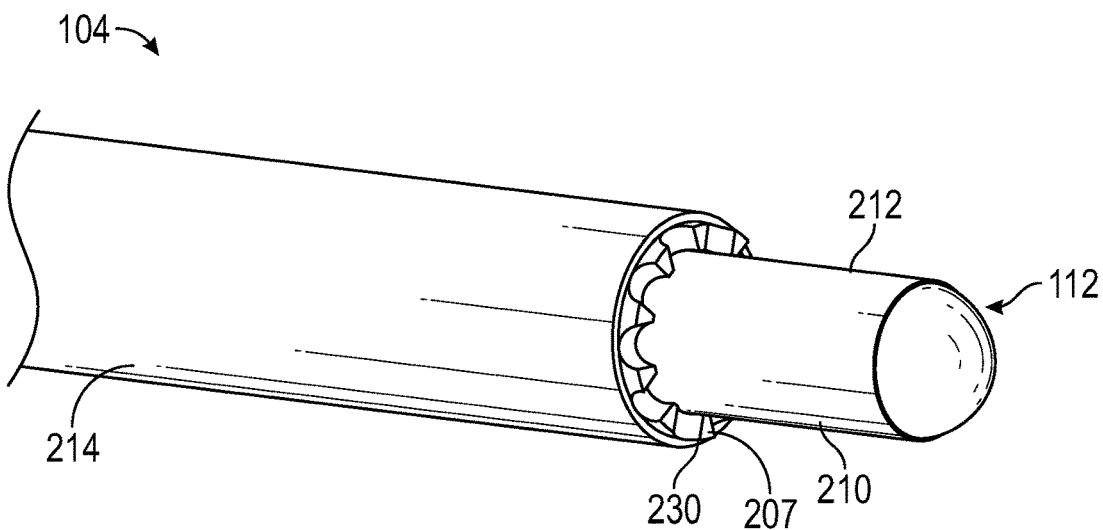

FIGS. 5A-5C illustrate a modified distal end face of the cannula 206. At least one distal extension 240 is carried by the cannula 206, to provide a site of enhanced energy density on the leading charge transfer surface 207 carried by the projection 240. At least two or four or more projections 240 may be provided, such as 10 as illustrated in FIG. 5B, creating scalloped surface with a plurality of circumferentially spaced apart distal transfer surfaces 207.

One method of delivering a large bore catheter in a single pass using the transseptal puncture system of the present invention may be as follows.
1. Advance a guidewire (GW) into the superior vena cava (SVC) and deliver a large bore catheter (e.g., left atrial appendage occlusion device; mitral valve repair or replacement; intra atrial adjustable annuloplasty device) with a dilator to the SVC.
2. Withdraw GW inside of the dilator.
3. Withdraw the large bore sheath and the dilator down to the right atrium.
4. Steer the sheath and dilator into position in the interatrial septum, specifically tenting the septum with the dilator.
5. Deliver the cannula and GW into position with the cannula extending distally beyond the dilator and the GW distally beyond the cannula and in contact with the fossa ovalis.
5a. If necessary for positioning purposes, withdraw cannula proximal to the bend of the steerable sheath, then step 6.
6. Activate the distal tip of the GW with RF energy, and pass the GW through the septum and into the left atrium (LA).
7. Drive the cannula, dilator and sheath distally through the septum and into the LA.
8. If the cannula cannot pass through the septum into the LA, activate the distal tip of the cannula with RF energy and advance the cannula into the LA.
9. Drive the dilator and the large bore sheath over the access cannula and into the LA.
10. Withdraw the cannula and dilator, and introduce the index procedure catheter through the large bore sheath.

As will be appreciated by those of skill in the art, the GW and cannula can alternatively be simultaneously operated in monopolar mode; either the GW or cannula can be energized separately; or the GW and cannula can be operated in bipolar mode, depending upon the desired clinical performance.

Figure 6:
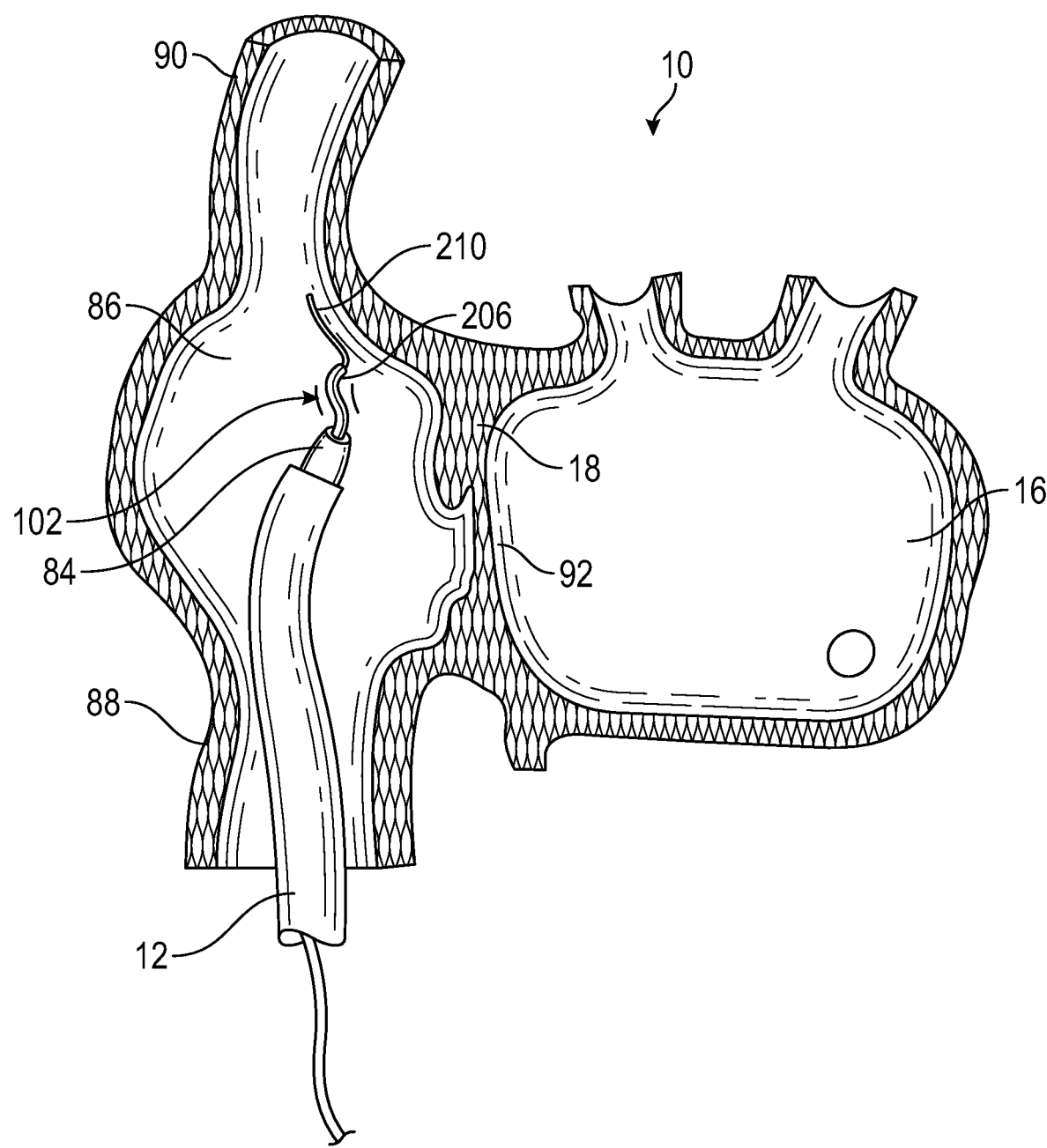
FIG. 6 is a schematic cross section of a portion of a human heart, having a transseptal crossing system of the present invention positioned in the right atrium.

Thus, referring to FIG. 6, there is illustrated a schematic cross-section of a portion of the heart 10. The right atrium 86 is in communication with the inferior vena cava 88 and the superior vena cava 90. The right atrium 86 is separated from the left atrium 16 by the intraatrial septum 18. The fossa ovalis 92 is located on the intraatrial septum 18. As seen in FIG. 6, a large bore transseptal sheath 12 may have a dilator 84, both riding over the cannula 206 and guidewire 210, all positioned within the right atrium 86.

Figure 7:
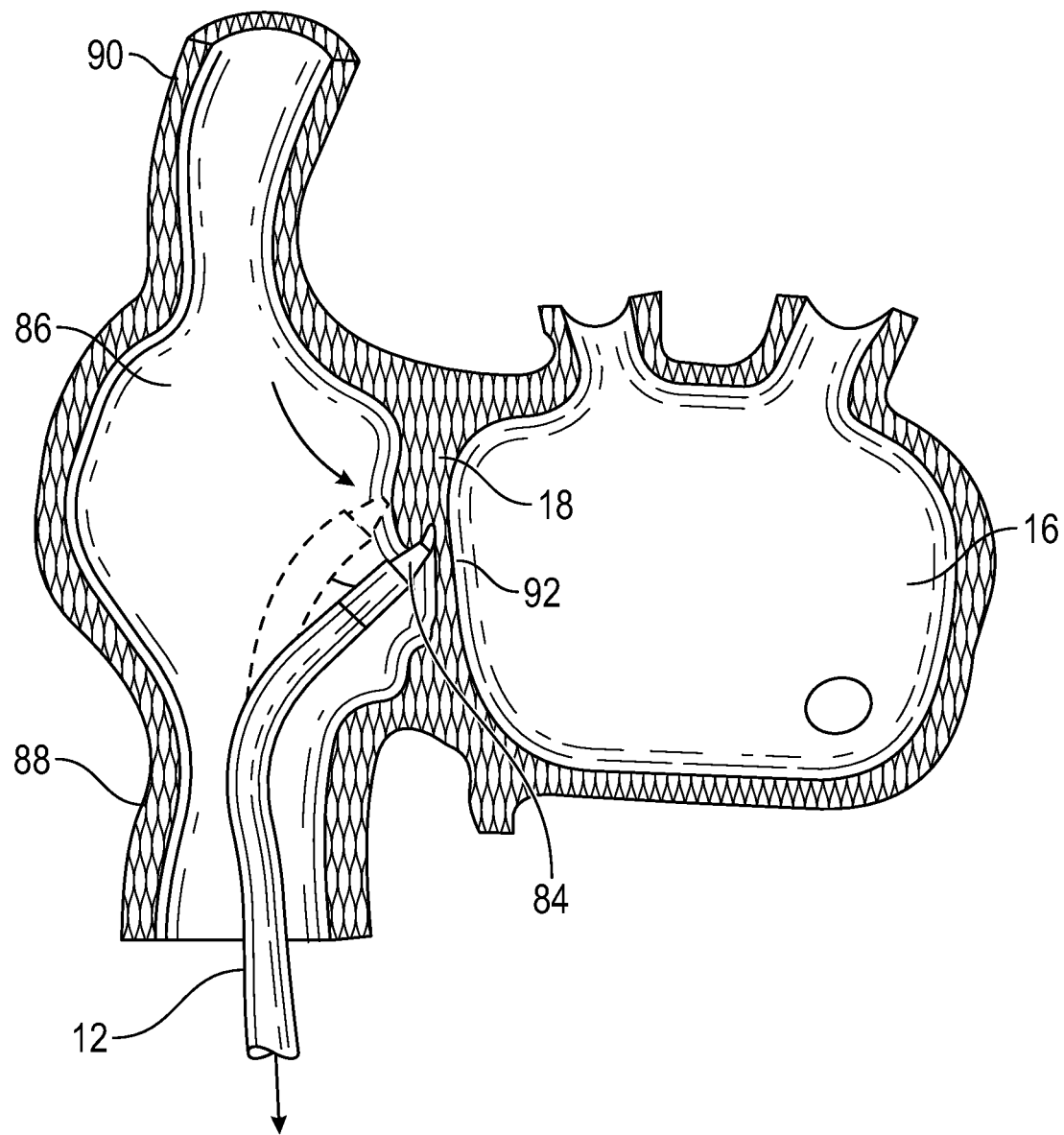
FIG. 7 is a view as in FIG. 6, showing positioning of the distal tip of the transseptal crossing system at the fossa ovalis.

The combination of the sheath 12 with the dilator 84 having the transseptal cannula 206 and GW 210 extending distally therefrom, is then drawn proximally from the superior vena cava while a curved section of the sheath, alone or in combination with a preset curve at the distal region of dilator 84 and or cannula 206, causes the tip of the cannula-GW combination to "drag" along the wall of the right atrium 86 and the septum 18, by proximal traction until the tip pops onto the fossa ovalis 92, as shown in FIG. 7.

Figure 8:
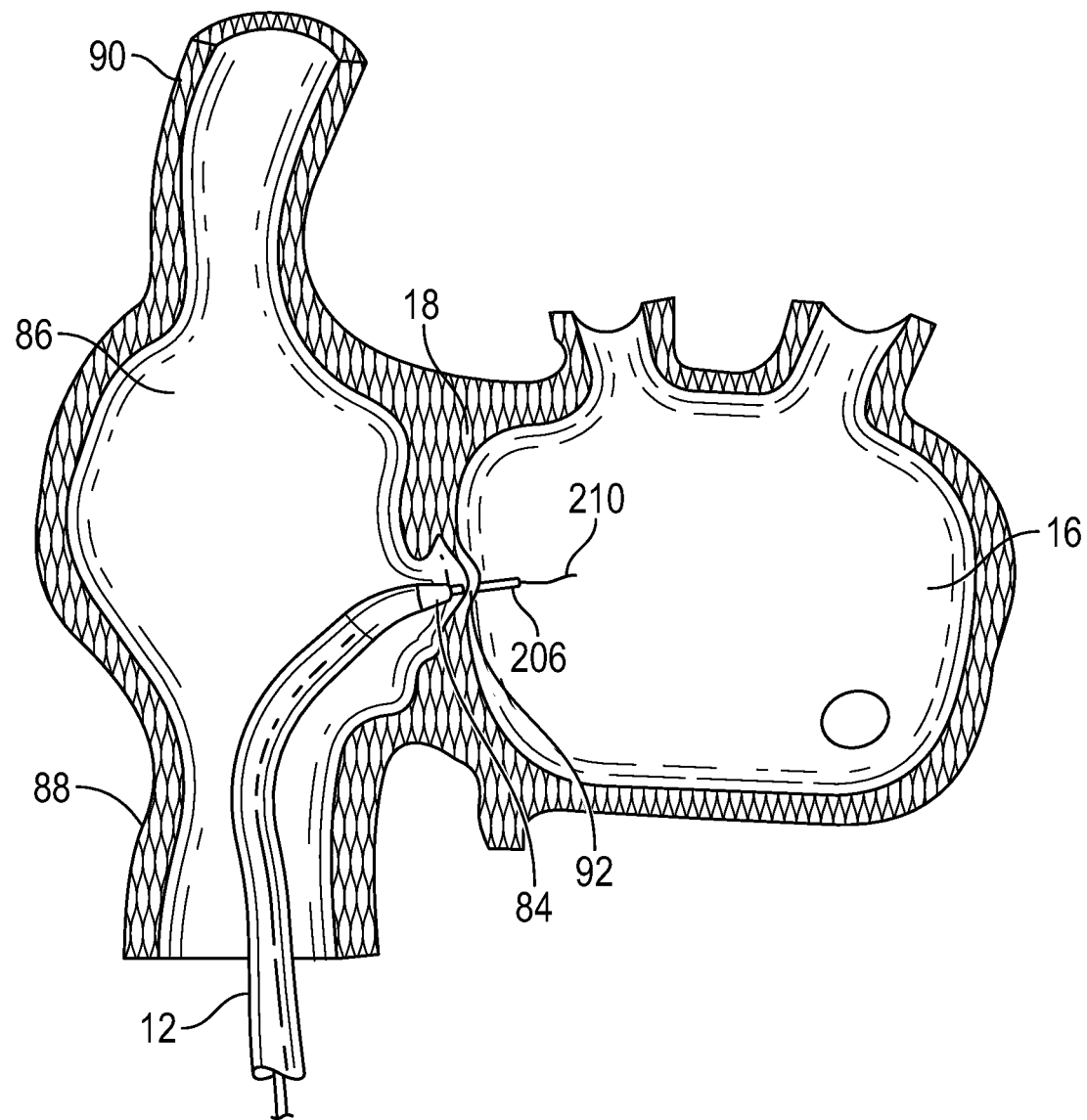
FIG. 8 shows penetration of the guidewire and cannula through the fossa ovalis.

After the tip of the cannula-GW combination has been placed in the desired location against the fossa ovalis 92, RF energy is applied via the tip of the transseptal GW 210 to allow the GW 210 to pass through the septum into the LA. As previously described, RF energy may also be delivered via the distal end of the cannula 206 if desired. See FIGS. 8 and 9.

One medical technique is to confirm the presence of the tip of the transseptal GW 210 within the left atrium 16. Confirmation of such location of the tip of the transseptal GW 210 may be accomplished by monitoring the pressure sensed through a transseptal GW lumen or an annular lumen defined between the GW 210 and the inside surface of the cannula 206 central lumen to ensure that the measured pressure is within the expected range and has a waveform configuration typical of left atrial pressure. Alternatively, proper position within the left atrium 16 may be confirmed by analysis of oxygen saturation level of the blood drawn through an available lumen; i.e., aspirating fully oxygenated blood. Finally, visualization through fluoroscopy alone, or in combination with the use of dye, may also serve to confirm the presence of the tip of the transseptal cannula 206 and GW 210 in the left atrium 16.

Figure 9:
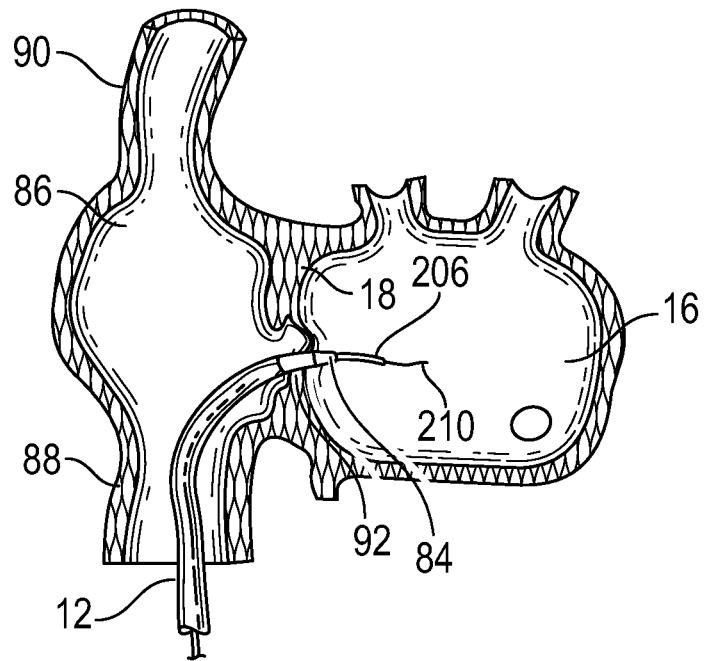
FIG. 9 shows penetration of the large bore sheath and dilator crossing the fossa ovalis.
Figure 10:
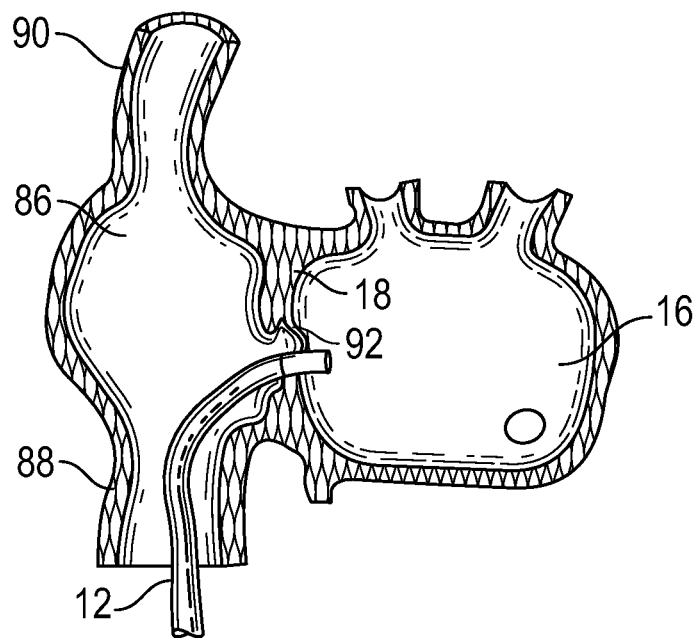
FIG. 10 shows the large bore sheath in position across the septum with the dilator and other system components removed to provide access to the left atrium.

After placing the transseptal cannula tip within the left atrium 16, the tip of the dilator 84 is advanced through the septum 18 and into the left atrium 16, as shown in FIG. 9. When the tapered tip of dilator 84 appears to have entered the left atrium 16, the transseptal cannula 206 may be withdrawn. The large bore sheath 12 may then be advanced into the left atrium 16, either by advancing the sheath 12 alone over the dilator 84 or by advancing the sheath 12 and dilator 84 in combination. The dilator 84 may then be withdrawn from sheath 12 when the latter has been advanced into the left atrium, thus leaving the main lumen of sheath 12 as a clear pathway to advancing further large bore diagnostic or therapeutic instruments into the left atrium.

What is claimed is:
1. A single pass, large bore transseptal crossing catheter system, comprising: an elongate, flexible tubular body having a proximal end, a distal end, and an electrically conductive sidewall defining a central lumen, the flexible tubular body being configured to be maneuverable through a patient's vasculature; a first insulation layer surrounding the electrically conductive sidewall and leaving exposed a first distal electrode tip being positioned on a distally facing end surface of the electrically conductive sidewall; an inner conductive wire having a second distal electrode tip, axially movably extendable through the central lumen; a second tubular insulation layer in between the inner conductive wire and the electrically conductive sidewall, wherein the second tubular insulation layer is separate from the first insulation layer; and wherein the second tubular insulation layer is disposed on an inner diameter of the electrically conductive sidewall.

2. The single pass system as in claim 1, wherein the first distal electrode tip comprises an annular conductive surface at the distal end of the tubular body.

3. The single pass system as in claim 2, wherein the second distal electrode tip is concentrically extendable through the annular conductive surface.

4. The single pass system as in claim 1, wherein the first distal electrode tip comprises at least one distal projection.

5. The single pass system as in claim 1, wherein the first distal electrode tip comprises a scalloped distal surface.

6. The single pass system as in claim 2, wherein the second distal electrode tip comprises a smooth, hemispherical surface.

7. The single pass system as in claim 1, further comprising an annular lumen extending between the tubular body and the inner conductive wire.

8. The single pass system as in claim 1, wherein the inner conductive wire includes a central lumen.

9. The single pass system as in claim 1, wherein the electrically conductive sidewall comprises a stainless steel tube.

10. The single pass system as in claim 4, comprising at least four distal projections.

11. The single pass system as in claim 1, wherein the tubular body has an outside diameter of about 0.050 inches.

12. The single pass system as in claim 11, wherein the inner conductive wire has an outside diameter of about 0.035 inches.

13. The single pass system as in claim 1, wherein the tubular body comprises an outside diameter of at least about 0.040 inches.

14. The single pass system as in claim 1, wherein the tubular body comprises an outside diameter of at least about 0.045 inches.

15. The single pass system as in claim 1, having sufficient structural integrity to guide a large bore catheter transvascularly through a septal wall and into a left atrium of a heart without breaking.

16. The single pass system as in claim 13, in which no part of the electrically conductive sidewall is a braided or woven wire.

17. The single pass system as in claim 1, wherein the second distal electrode tip is configured to extend beyond the tubular insulation layer.

18. The single pass system as in claim 1, wherein the second distal electrode tip is configured to contact and ablate tissue.

19. The single pass system as in claim 1, wherein the inner conductive wire is flexible.

20. The single pass system as in claim 1, wherein the inner conductive wire is configured to be withdrawn from the central lumen.

* * * * *